(12) United States Patent
De Vries et al.

(10) Patent No.: US 7,884,223 B2
(45) Date of Patent: Feb. 8, 2011

(54) CHIRAL COMPOUND SUITABLE AS A CATALYST FOR ASYMMETRIC TRANSFER HYDROGENATION

(75) Inventors: Johannes Gerardus (Hans) De Vries, Maastricht (NL); Gerardus Karel Maria Verzijl, Well (NL); Andreas Hendrikus Maria De Vries, Maastricht (NL); Vincent Ritleng, Strasbourg Cedex 2 (FR); Adeline Marie Joseèphe Voelklin, Heidelberg (DE)

(73) Assignee: DSM IP Assets B.V., Heerlen (NL)

( * ) Notice: Subject to any disclaimer, the term of this patent is extended or adjusted under 35 U.S.C. 154(b) by 768 days.

(21) Appl. No.: 11/667,381

(22) PCT Filed: Nov. 10, 2005

(86) PCT No.: PCT/EP2005/012198

§ 371 (c)(1),
(2), (4) Date: Nov. 1, 2007

(87) PCT Pub. No.: WO2006/050988

PCT Pub. Date: May 18, 2006

(65) Prior Publication Data

US 2008/0269529 A1  Oct. 30, 2008

(30) Foreign Application Priority Data

Nov. 11, 2004  (EP)  .................................. 04078106

(51) Int. Cl.
*C07F 15/00* (2006.01)
*B01J 31/00* (2006.01)

(52) U.S. Cl. ........................ 556/137; 556/140; 568/814; 502/155

(58) Field of Classification Search ................. 556/137, 556/140; 568/814; 502/155
See application file for complete search history.

(56) References Cited

FOREIGN PATENT DOCUMENTS

EP  0 916 637 A1  6/1996

OTHER PUBLICATIONS

Vincent Ritleng et al., "Reaction between Ethylene and Cycloruthenated Tertiary Amines: Stoichiometric Olefin Arylation and Stereospecific One-Carbon-Atom Insertion", Organometallics, vol. 22, 2003, pp. 347-354.

M. J. Palmer, et al., "Asymmetric transfer hydrogenation of C=O and C=N bonds"; Dept. of Chemistry, Warwick University, Coventry, CV4 7AL. UK, Received Jan. 27, 1999; revised May 29, 1999, accepted Jun. 1, 1999.
E. Lindner, et al., "Asymmetric hydrogenation of an x,B-unsaturated ketone by diamine(ether-phosphine)ruthenium(ll) complexes and lipase-catalyzed kinetic resolution: a consecutive approach"; Tetrahedron: Asymmetry 14 (2003) 1045-1053.
S. Fernandez, et al., "An Effective Route to Cycloruthenated N-Ligands under Mild Conditions"; Organometallics 1999, 18, 2390-2394.
N. Gul, et al., "Synthesis, Characterization, and Diastereoselectivity of Chloride Substitution Reactions of Cycloruthenated (R)c-(+)-N,N-Dimethyl-a-(2-naphthy1) Ethyiamine"; Organometallics 1999 18, 709-725.
S. Attar, et al., "Mettalacycles with Stereogenic Metal Centers: Synthesis and Characterization of Diastereomeric Cycloruthenated Chiral Amines"; Organometallics 1995, 14, 4559-4569.
S. Attar, et al., "Diastereoselectivity of Chloride Substitution Reactions of Cycloruthenated (R)c-(+)- and (S)c-(-)-Dimethyl(1-phenylethyl)amine"; Organometallics 1996, 15 2932-2946.
G. Martin, et al., "Synthesis of Ruthenium Amide Complexes by Nucleophllic Attack on Ortho-Metalated Imine Ligands", Organometallics 1991, 10, 2804-2811.
PCT Written Opinion of the International Searching Authority; dated Nov. 11, 2004.
PCT International Search Report; dated Oct. 11, 2005 (PCT/EP2005/012198).
M. J. Palmer, et al., "Asymmetric transfer hydrogenation of C=O and C=N bonds"; Tetrahedron: *Asymmetry* 10 (1999) 2045-2061.

*Primary Examiner*—Porfirio Nazario Gonzalez
(74) *Attorney, Agent, or Firm*—Nixon & Vanderhye P.C.

(57) ABSTRACT

The invention relates to an enantiomerically enriched chiral compound comprising a transition metal M, which comprises four, five or six coordinating groups of which at least one pair is linked together to form a bidentate ligand, in which M is directly bound via one single σ-bond to a carbon atom of an optionally substituted and/or optionally fused (hetero)aromatic ring of said bidentate ligand and in which M is directly bound to a nitrogen atom of a primary or secondary amino group of said bidentate ligand, thereby forming a metallacycle between said bidentate ligand and the metal M, said metal M being selected from the metals of groups 8 and 9 of the Periodic Table of the Elements, in particular iron, ruthenium, osmium, cobalt, rhodium, or iridium. The chiral compound can be used as a catalyst, preferably in an asymmetric transfer hydrogenation process. The invention further relates to a process for an asymmetric transfer hydrogenation of a prochiral compound in the presence of a hydrogen donor and the chiral compound of the invention comprising a transition metal chosen from the metals of groups 8, 9 and 10 of the Periodic Table, in particular iron, ruthenium, osmium, cobalt, rhodium, iridium, nickel, palladium or platinum as the catalyst.

11 Claims, No Drawings

CHIRAL COMPOUND SUITABLE AS A CATALYST FOR ASYMMETRIC TRANSFER HYDROGENATION

This application is the US national phase of international application PCT/EP2005/012198 filed 10 Nov. 2005 which designated the U.S. and claims benefit of EP 04078106.4, dated 11 Nov. 2004, the entire content of which is hereby incorporated by reference.

The invention relates to an enantiomerically enriched chiral compound comprising a transition metal compound M, which comprises four, five or six coordinating groups. The invention further relates to the use of said compound as a catalyst and to a process for the preparation of a variety of enantiomerically enriched compounds via asymmetric transfer hydrogenation using the catalyst according to the invention.

Asymmetric transfer hydrogenation is a method for the preparation of an enantiomerically enriched compound in which the presence of a transition metal catalyst comprising an enantiomerically enriched ligand (also defined as "optically active" ligand) ensures that the double bond of a prochiral compound is asymmetrically reduced through hydrogen transfer with a hydrogen-donating organic compound (hereby defined as the hydrogen donor). The general advantage of such an asymmetric transfer hydrogenation is that this reaction can take place under relatively mild conditions as regards to temperature and pressure while the yield is relatively high and the by-product content low, so that the production costs can be low. In practice, this asymmetric transfer hydrogenation is often employed for the preparation of enantiomerically enriched alcohols from prochiral ketones.

The term "enantiomerically enriched compound" means that one of the enantiomers of the compound is present in excess compared to the other enantiomer. This excess will hereinafter be referred to as "enantiomeric excess" or e.e. (as for example determined by chiral GLC or HPLC analysis). The enantiomeric excess e.e. is equal to the difference between the amounts of enantiomers divided by the sum of the amounts of the enantiomers, which quotient can be expressed as a percentage after multiplication by 100.

EP 0 916 637 A1 discloses such chiral compounds that are used as catalysts for the asymmetric transfer hydrogenation. Other similar catalysts are described in: M. J. Palmer and M. Wills, Tetrahedron: Asymmetry, 1999, 10, 2045-2061. These known catalysts comprise a transition metal, which is chosen from group VIII of the periodic system, this preferably being ruthenium, with an enantiomerically enriched diamine, amino alcohol or aminophosphine ligand as a bidentate ligand. The disadvantage of the known chiral compounds/catalysts is that these are based on ligands which in general are expensive due to their rather difficult and/or elaborate synthesis. Many synthetic steps may be needed to prepare the catalysts disclosed in EP 0 916 637 A1 or the known catalysts are not easily obtained in enantiomerically pure form. Moreover, none of the ligands and catalysts described in the prior art can be prepared in great variety in a relatively short period of time.

It is the object of the present invention to provide a chiral compound that can be easily constituted from readily available ligands or coordinating groups and thus can be made in great variety in an acceptable number of synthetic steps. It is a further object of the invention to provide a chiral and enantiomerically enriched catalyst, in particular for asymmetric transfer hydrogenation, that shows acceptable activity.

This object is achieved according to the invention by using a chiral compound comprising a transition metal compound M, which comprises four, five or six coordinating groups, wherein at least one pair of said coordinating groups is linked together forming a bidentate ligand, in which M is directly bound via one single σ-bond to a carbon atom of an optionally substituted and/or optionally fused (hetero)aromatic ring of said bidentate ligand and in which M is directly bound to a nitrogen atom of a primary or secondary amino group of said bidentate ligand, said metal M being selected from the metals of groups 8 and 9 of the Periodic Table of the Elements, in particular iron, ruthenium, osmium, cobalt, rhodium, or iridium. Particularly, the bidentate ligand and the metal M are forming a metallacycle. This bidentate ligand of the chiral compound of the invention is hereinafter referred to as a cyclometallated or cyclometallatable ligand.

With the term "coordinating group" is meant that the group is capable of binding with a transition metal atom or ion, preferably by donating electron density to a transition metal atom or ion. The terms "coordinating group or atom" and "ligand" are interchangeably used throughout the present application. With the term "a bidentate ligand" is meant a ligand comprising two coordinating atoms or groups which bind on a transition metal M, said two coordinating groups being linked together forming a bidentate ligand.

In particular, the cyclometallatable ligand in the chiral compound according to the present invention contains as a first coordinating group said carbon atom of an optionally substituted and/or optionally fused (hetero)aromatic ring and as a second coordinating group said nitrogen atom of a primary or secondary amino group. In addition to this cyclometallatable ligand, the chiral compound according to the invention may additionally contain two, three or four coordinating groups which may be linked together in pairs to form one or more additional bidentate ligands, i.e. ligands comprising two coordinating atoms or groups which bind on a transition metal M, wherein the coordinating atoms may be chosen from P, N, C, O or S. The one or more additional bidentate ligands may also be a cyclometallatable ligand as defined throughout this invention. Preferably, the chiral compound of the invention comprises not more than one additional bidentate ligand. The additional ligand may also be a tridentate or tetradentate ligand, i.e. a ligand wherein three, respectively four coordinating atoms or groups are bound to the metal M, said three/four coordinating groups—to be chosen from P, N, C, O or S— being linked together forming a tri-/tetra-dentate ligand. The tridentate ligand cannot be a 'Pincer' ligand, i.e. a ligand that contains an aromatic ring sigma-bonded via a carbon atom to the metal M and contains two additional coordinating groups bound to the metal. Preferably, the chiral compound of the invention does not contain a tridentate ligand.

The advantage of the chiral compounds of the present invention is that these compounds are easily accessible, since the coordinating groups, in particular the cyclometallatable ligand can be easily prepared in a limited number of synthetic steps. For industrial use it is important that a large "library" of coordinating groups/ligands (a great variety of ligands that belong to the same family, i.e. they share some structural characteristics) is available to increase the chance of finding a suitable catalyst for a given transformation. Also for use in production of pharma intermediates it is important that the chiral compound can be prepared on kilogram-scale in a relatively short period of time as time-to-market should be as short as possible when processes for the production of new drugs are developed.

Surprisingly, when the chiral compound of the invention is in enantiomerically enriched form, the compound is highly suitable as a catalyst, in particular for asymmetric transfer hydrogenation, because of it's relatively high activity. This is particularly unexpected as these compounds have never been made before. Moreover, fast high throughput screening is possible.

Preferably, the chiral compound of the invention may be represented by any one of the formulae 1a, 1b or 1c, depending on whether the transition metal contains four, five or six coordinating groups,

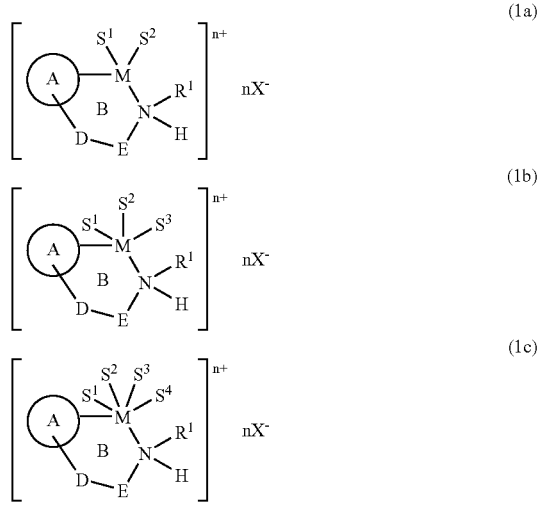

wherein A, B, D, E, $S^1$ to $S^4$, $R^1$, X and n are as defined below and H is hydrogen.

The cyclometallatable bidentate ligand of the chiral compound according to formulae (1a) to (1c) comprises the optionally substituted and/or optionally fused (hetero)aromatic ring A and the amino group —$NR^1H$, wherein the nitrogen of the amino group is bound to the ring A via a fragment D-E. Said cyclometallatable bidentate ligand, when bound to the metal M, is forming a metallacycle, represented in particular by ring B. In formulae (1a) to (1c), X is a non-coordinating anion, n is an integer chosen from 0, 1 or 2; $S^1$, $S^2$, $S^3$ and $S^4$ are coordinating groups, and M may be selected from the metals of groups 8 and 9 of the Periodic Table, in particular iron, ruthenium, osmium, cobalt, rhodium, or iridium.

Ring A is an optionally substituted and/or fused (hetero) aromatic ring such as, for example, an optionally substituted benzene, thiophene, furan, pyrrole, and the like. Suitable examples of a fused (hetero)aromatic ring A may be an optionally substituted naphthalene, tetraline, phenanthrene, anthracene, fluorene, benzofuran, benzothiophene, dibenzothiophene, indole, cyclohexenopyrrole. Ring A may for example also have an aromatic sandwich structure, such as an optionally substituted ferrocene, cobaltocene or ruthenocene. The use of an optionally substituted benzene or an optionally substituted naphthalene as ring A is preferred. The metal M can be bound via one single sigma bond to any carbon atom of ring A where this is chemically feasible.

Ring B may be an optionally substituted and/or optionally fused (hetero)aliphatic ring. Ring B may be fused to a further (hetero)aromatic or (hetero)aliphatic ring as long as this further ring does not contain a metal M. A third ring may fuse rings A and B in formulae 1a-1c together, as long as this third ring does not contain the metal M, preferably does not contain any metal.

The fragment D-E-$NR^1H$ is preferably attached to ring A in such a way that it can easily form ring B. Preferably, ring B is substantially stable under the chosen reaction conditions, more preferably ring B is substantially stable during the reaction time of a catalytic reaction, preferably an asymmetric transfer hydrogenation reaction. The fragment D-E-$NR^1H$ could for example be situated in the ortho position with respect to the carbon atom of ring A which binds to the metal, or in the ipso position if ring A is a fused ring. It may even be situated on the third most remote ring if ring A is tricyclic as long as the nitrogen atom can bind to the metal. Other possibilities are known to a person skilled in the art.

Each of D and E may be independently chosen from the group consisting of a bond, an optionally substituted methylene group $CR^2R^3$, an optionally substituted ethylene group $CR^4R^5CR^6R^7$, an optionally substituted vinyl group $CR^8=CR^9$, said $CR^8=CR^9$— group optionally being part of an aromatic ring, or a heteroatom, the latter preferably selected from the group consisting of oxygen or sulphur, SO or $SO_2$. E is preferably a carbon atom or group and preferably, E is not a heteroatom. In case D is a bond, E is directly bound by one single sigma-bond to ring A. In case E is a bond, D is directly bound by a single sigma-bond to the nitrogen atom of the amino group, and in case both D and E represent a bond, ring A is directly bound via a single sigma-bond to the nitrogen atom. In the latter case, ring B is a four-membered ring, when the nitrogen atom is situated in ortho position with respect to the carbon atom of ring A. According to a preferred embodiment of the present invention, D and E are not both a bond at the same time.

If one of D or E is a substituted methylene $CR^2R^3$, the two substituents, $R^2$ and $R^3$ may be different, making the substituted methylene group chiral. The same is true if $R^4$ and $R^5$ are different and if $R^6$ and $R^7$ are different. Preferably, at least one of D or E is chiral or contains a chiral substituent. If D and E are both a methylene, or both an ethylene, or both a vinyl group, their substituents $R^2$ to $R^9$ may be different from each other.

$R^1$, $R^2$, $R^3$, $R^4$, $R^5$, $R^6$, $R^7$, $R^8$ and $R^9$ may each independently be selected from the group consisting of hydrogen, an optionally substituted carbon substituent, an optionally substituted oxygen substituent, or an optionally substituted nitrogen substituent. Suitable examples of an optionally substituted carbon substituent may for example be an optionally substituted alkyl group with 1-20 carbon atoms, an optionally substituted (hetero)aromatic group with 1-25 carbon atoms, which may be fused, a nitrile, a carbamoyl group, such as carbamoyl or N-methyl-carbamoyl, and the like. Suitable examples of optionally substituted alkyl groups are methyl, ethyl, propyl, butyl, isopropyl, cyclopropyl, cyclobutyl, cyclopentyl, cyclohexyl, tert-butyl, (S)- and (R)-isobutyl, 2-methoxyethyl, 2-ethoxy-ethyl, benzyl, cyclohexyl, (R)- and (S)-1-phenyl-ethyl, 2-phenylethyl, (R)- and (S)-1-naphth-1-yl-ethyl, (R)- and (S)-1-naphth-2-yl-ethyl, and the like. Suitable aromatic groups are phenyl, p-chlorophenyl, meta-methoxy-phenyl, ortho-toluoyl, para-trifluoromethylphenyl, naphthyl, 6-methoxy-naphth-2-yl, 2- or 3-thiophenyl, 1- or 2-indenyl, 1- or 2-furyl, and the like. Suitable examples of an optionally substituted oxygen substituent may be an alkanoyl such as acetyl or benzoyl, an alkoxy group, such as for example methoxy, ethoxy, benzyloxy, and the like, an ester group such as for example ethoxycarbonyl, and the like. Suitable examples of an optionally substituted nitrogen substituent may be, for example an amino group, an alkyl amino such as benzyl amino, a dialkylamino such as dimethylamino, an amidogroup, such as for example acetamido, a nitro group, and the like. Additionally, $R^1$ may be a void, in which case the cyclometallatable ligand is di-anionic.

If D or E is a methylene group $CR^2R^3$, the two substituents $R^2$ and $R^3$ may be bound together leading to the formation of a ring, which ring has a spiro relationship to ring B. $R^1$ may be bound together with one of $R^2$ to $R^9$, so that they form a ring. Each of the substituents $R^2$ to $R^9$ may individually bind with one of the other substituents $R^2$ to $R^9$, so that they form a ring. This ring can be saturated, unsaturated or aromatic.

The coordinating groups $S^1$, $S^2$, $S^3$ and $S^4$ may each independently be anionic or neutral groups, or may be hydride, a halide or a void, with the proviso that only one or two of $S^1$, $S^2$, $S^3$ or $S^4$ can be anionic, hydride, a halide or a void. Suitable coordinating groups $S^1$, $S^2$, $S^3$ and $S^4$ may be independently chosen from, for example, a halide, in particular chloride, bromide, fluoride or iodide; a neutral ligand, such as a phosphorus containing ligand, for instance a phosphine ligand, such as triphenylphosphine, or substituted variants thereof, such as tri-o-tolylphosphine; a phosphite, such as tri-phenyl phosphite or a substituted variant thereof, such as tri-o-tolyl phosphite; a phosphonite, such as diphenyl phenylphosphonite or substituted variants thereof, a phosphinite such as phenyl diphenylphosphinite or a phosphoramidite such as enantiomerically enriched [2-N,N-dimethylamino] dinaptho[2,1-d:1',2'-f][1,3,2] dioxaphosphepin; a nitrogen containing ligand, such as optionally substituted pyridine, triazole or bipyridine; CO; a nitrile, such as acetonitrile or benzonitrile; a solvent, such as dmso, ether or THF, an anionic ligand such as cyclopentadienyl, pentamethylcyclopentadienyl, indenyl, fluorenyl, 1-hydroxy, 2,3,4,5-tetraphenylcyclopentadienyl, p-toluenesulfonate, acetate or trifluoroacetate; an optionally substituted olefin such as ethylene, maleic anhydride, or benzoquinone; an optionally substituted diene such as norbornadiene or cyclooctadiene; an aromatic ligand, which will usually be bound in eta-6 fashion such as benzene, o-cymene, p-cymene, m-cymene, cumene or naphthalene, or a void. In case one pair of $S^1$ and $S^2$ forms a bidentate ligand, the two coordinating atoms may be different or the same. One or more of $S^1$, $S^2$, $S^3$ and $S^4$ may be chiral, preferably enantiomerically enriched. Preferably, at least one of $S^1$, $S^2$, $S^3$ or $S^4$ is an aromatic compound, more preferably an aromatic compound which is bound to the metal M in eta-6 fashion, even more preferred benzene, cyclopentadienyl (Cp), or pentamethylcyclopentadienyl (Cp*). Further preferred, at least one of $S^1$, $S^2$, $S^3$ or $S^4$ is a solvent molecule, preferably an organic solvent molecule, such as for example acetonitrile ($CH_3CN$), tetrahydrofuran (THF), and the like.

Suitable examples of the non-coordinating anion X may be $BF_4$, $PF_6$, $ClO_4$, a sulfonate, a triflate, BARF and the like, more preferably X is $BF_4$ or $PF_6$.

According to a preferred embodiment of the present invention, the chiral compound is in enantiomerically enriched form, in particular when used as a catalyst, preferably to catalyse asymmetric transfer hydrogenation reactions.

Preferably, the catalyst of the invention has an e.e. of at least about 30%, preferably at least about 40%, more preferred at least about 50%, even more preferred at least about 70%, particularly preferred at least about 90%, and most preferred at least about 95%. It is even possible to prepare a catalyst in an e.e. of higher than about 98%.

Preferably, (i) at least one of the atoms of and/or at least one of the substituents on said cyclometallatable ligand of the catalyst of the invention is chiral and enantiomerically enriched, or (ii) at least one of the coordinating groups $S^1$, $S^2$, $S^3$ or $S^4$ of the catalyst of the invention is chiral and enantiomerically enriched, or (iii) the metal M is chiral and enantiomerically enriched, wherein at least one of the situations (i), (ii) or (iii) applies. Any combination of two or more of the options (i), (ii) and (iii) may apply at the same time.

Within embodiment (i) of the invention, preferably the fragment D-E-$NR^1$H— is chiral and enantiomerically enriched. This means that at least one of D, E or $NR^1$H— is chiral or contains a chiral substituent. In case $R^1$ is a carbon, oxygen, phosphorus or nitrogen substituent, $R^1$ may be chiral. More preferably, at least one of D or E is chiral or contains a chiral substituent.

According to embodiment (ii) of the invention, at least one of the coordinating groups $S^1$, $S^2$, $S^3$ or $S^4$ in formulae (1a)-(1c) is chiral and enantiomerically enriched.

The present invention further relates to a process for the preparation of the chiral compound according to any one of formulae 1a, 1b or 1c, in particular a process as depicted in Scheme 1:

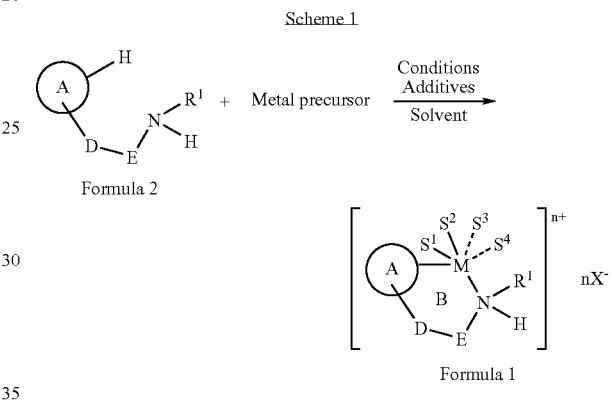

The dotted line in formula 1 of Scheme 1 is used to represent each of the compounds 1a, 1b and 1c of the invention.

Said process comprises reacting a metal precursor comprising a transition metal chosen from groups 8 and 9 of the Periodic Table, in particular iron, ruthenium, osmium, cobalt, rhodium, or iridium with a cyclometallatable bidentate ligand according to formula 2, preferably in the presence of a solvent and if desired, an additive.

A comparable synthesis process has been described in S. Fernandez, M. Pfeffer, V. Ritleng and C. Sirlin, *Organometallics*, 1999, 18, 2390 for catalysts comprising a ruthenium metal with a tertiary amine coordinating group, which is incorporated herein by reference.

Either the metal precursor and/or the solvent and/or the additives used may comprise one, more or all four of the $S^1$, $S^2$, $S^3$ and $S^4$ groups. According to a preferred embodiment, at least one of $S^1$ to $S^4$ is an aromatic group bound to the metal in η6-fashion, preferably being introduced via the metal precursor.

Examples of the cyclometallatable ligand of formula 2 are given in FIG. 1 below. Whereas only one configuration is depicted it will be clear that the cyclometallatable ligand with the opposite configuration can also be used. Both primary and secondary amines can function as the cyclometallatable bidentate ligand of formula 2. In addition, it will be possible to convert the primary amines according to formula 2 into a great variety of secondary amines according to formula 2, for example by alkylation with different alkyl halides or the like, by reductive amination with different aldehydes or ketones, or any other method known to a person skilled in the art. In this way, a limited number of chiral primary amines may be converted into a large number of secondary amines ("a library"), which increases the chance of finding a suitable catalyst for a given transformation. Reductive amination with aldehydes or ketones is heretofore preferred. Many methods exist for reductive amination, which are well-described in chemical literature.

One possible way to affect direct reductive amination is by reacting a primary amine with an aldehyde in the presence of NaCNBH$_3$. Another possible way to affect the reductive amination is by reacting a primary amine with a ketone in the presence of a titanium reagent, such as for example TiCl$_4$ or Ti(Oi-Pr)$_4$, and a reducing agent such as for example NaBH$_4$ or NaCNBH$_3$. A further possible way is to form an imine by reacting a primary amine with an aldehyde or ketone and in a next step reducing the imine to the secondary amine of formula 2 by using heterogeneous hydrogenation (Pd/C or Ra—Ni as catalyst) or with NaBH$_4$ or NaCNBH$_3$. A great variety of aldehydes or ketones may be used for such a reductive amination reaction, and is known to a person skilled in the art. The aldehydes and ketones can be either aliphatic or aromatic; they may also be chiral.

Figure 1

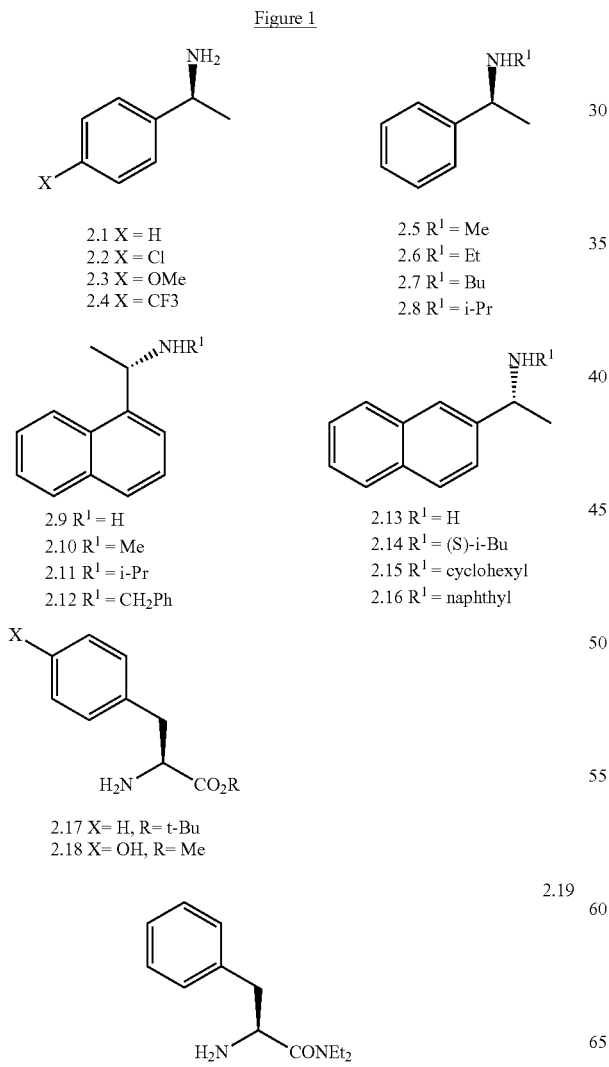

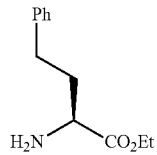
2.20

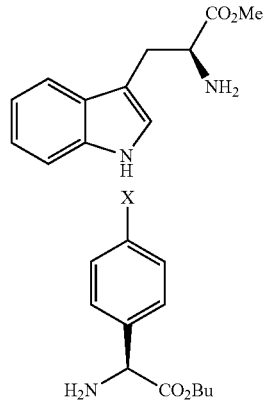
2.21

2.22 X = H
2.23 X = OH

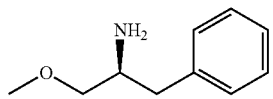
2.24

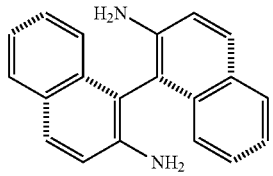
2.25

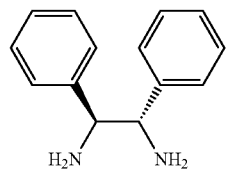
2.26

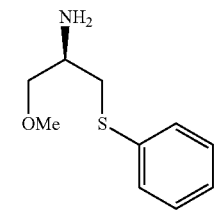
2.27

2.28 R$^1$ = H
2.29 R$^1$ = Me

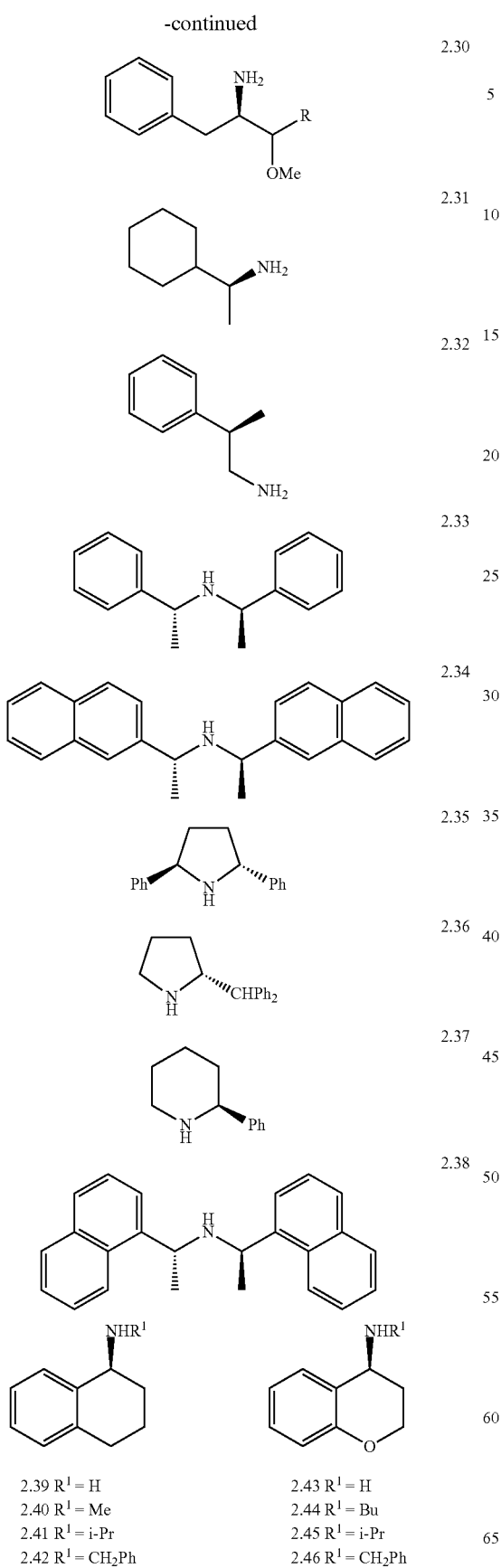
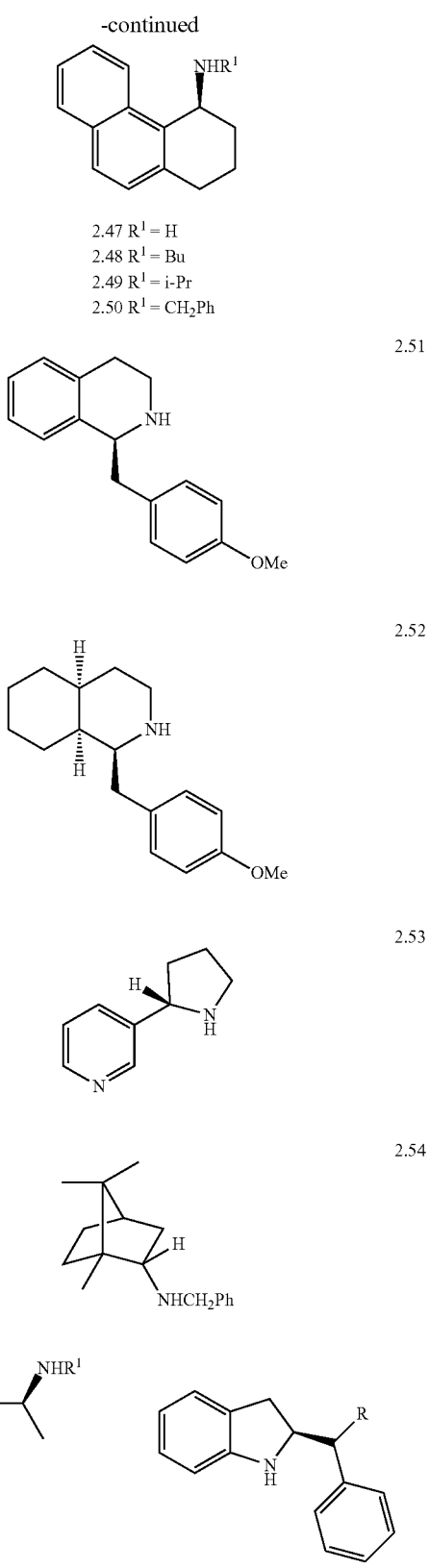

-continued

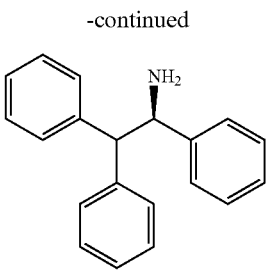

2.61

The chiral compounds/catalysts of the invention may be prepared by reacting the cyclometallatable ligand of formula 2 with a suitable metal precursor. Use is preferably made of a metal precursor of the general formula 3:

$$M_p G^1_q G^2_r Y_s \qquad (3)$$

wherein:

p, q, r and s each independently represent 0, 1, 2, 3, 4, 5, 6, . . . ;

M is a transition metal chosen from the metals from groups 8 and 9 of the Periodic Table, in particular the group consisting of iron, ruthenium, osmium, cobalt, rhodium, or iridium, most preferably ruthenium.

The metal precursor according to formula 3 may contain one, two or more of the coordinating groups $G^1$ and/or $G^2$, and each of $G^1$ or $G^2$ may independently be the same as described for $S^1$ to $S^4$ above. Some or all of the coordinating groups $G^1$ and $G^2$ may stay on the metal after formation of the chiral compound of formula 1, in which case they are identical to $S^1$ to $S^4$. However, the $G^1$ and $G^2$ groups may also dissociate from the complex during the reaction and, in that case, will not be present in the chiral compound of formula 1. The coordinating groups $S^1$ to $S^4$ in formula 1 may also stem from the solvent that is used during its formation or from the additive, which is added during its formation. The chiral compound of formula 1 may also be formed by an additional step of replacing any one of said coordinating groups $S^1$ to $S^4$ by another $S^1$ to $S^4$— group. This is particularly preferred when the particular coordinating group from $S^1$ to $S^4$ is chiral.

Y is a non-coordinating anion and may be the same as defined above for X or additionally, Y may be selected from carboxylates such as acetate, trifluoroacetate or benzoate; halogens, and the like.

Examples of suitable transition metal precursors according to formula 3 are $RuCl_3.nH_2O$, $[RuCl_2(\eta^6\text{-benzene})]_2$, $[RuCl_2(\eta^6\text{-cymene})]_2$, $[RuCl_2(\eta^6\text{-mesitylene})]_2$, $[RuCl_2(\eta^6\text{-hexamethylbenzene})]_2$, $[RuCl_2(\eta^6\text{-1,2,3,4-tetramethylbenzene})]_2$, $[RuBr_2(6\text{-benzene})]_2$, $[RuI_2(\eta^6\text{-benzene})]_2$, trans-$[RuCl_2(DMSO)_4]$, $RuCl_2(PPh_3)_3$, $Ru(COD)(COT)$, $IrCl_3$, $[Ir(COD)Cl]_2$, $[Ir(CO)_2Cl]_n$, $[IrCl(CO)_3]_n$, $[Ir(Cp^*)Cl_2]_2$, $Ir(Acac)(COD)$, $[Ir(NBD)Cl]_2$, $[Ir(COD)(C_6H_6)]^+BF_4^-$, $[(CF_3C(O)CHC(O)CF_3)Ir(COE)_2]$, $[Ir(CH_3CN)_4]^+BF_4^-$, $[Rh(C_6H_{10})Cl]_2$ (in which $C_6H_{10}$=hexa-1,5-diene), $[Rh(COD)Cl]_2$, $[Rh(Cp)(CO)_2]$, $[Rh(norbornadiene)_2]BF_4$, $[Rh(Cp^*)Cl_2]_2$ (in which Cp* is pentamethylcyclopentadienyl), $CoCl_2$, $Co(acac)_2$, $Co(acac)_3$, $Co_2(CO)_8$, $CpCo(CO)_2$, $Fe(acac)_2$, $FeCl_2.nH_2O$, $FeCl_3.nH_2O$, $[C_5H_5Fe(CO)_2]_2$, $Fe_3(CO)_{12}$, $Os_3(CO)_{12}$, $OsCl_3.nH_2O$, and the like.

Preferably, the process for preparing the chiral compound/catalyst of formulae 1a-1c comprises reacting the metal precursor of formula 3 with the cyclometallatable ligand of formula 2 in a suitable solvent, such as for example acetonitrile, dichloromethane, THF, ether, ethanol, methanol, toluene, EtOAc, and the like, of which acetonitrile is particularly preferred. In some cases the solvent may become part of the chiral compound of the invention. This may for example be the case when acetonitrile is used, since acetonitrile has been found to be a very suitable coordinating group S.

The molar ratio of the metal M to the cyclometallatable bidentate ligand of formula 2 is preferably chosen to be between 2:1 and 1:10, more preferably between 1:1 and 1:6.

This process may be effected at temperatures between 0-120° C., preferably between 20-100° C., more preferably between 20-80° C., even more preferred at room temperature.

The process is preferably performed under an inert atmosphere, such as for example nitrogen.

In some cases, for example as a source for the anion, or in order to influence the reaction equilibrium of the process of Scheme 1, it may preferred to add additives, such as acids, for example acetic acid or hydrogen chloride, bases, such as for example KOH, NaOH or $Et_3N$, phase transfer catalysts, such as for example $Bu_4NBr$ or salts of HX—wherein X has the same definition as above—such as for example $NaPF_6$ or $NaBF_4$.

Examples of chiral compounds of formula 1 are depicted in FIG. 2.

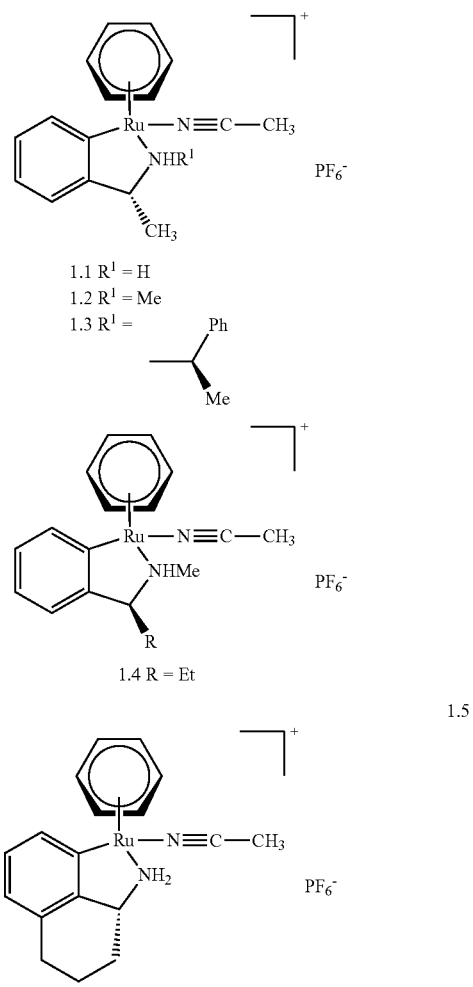

FIG. 2

1.1 $R^1$ = H
1.2 $R^1$ = Me
1.3 $R^1$ =

1.4 R = Et 1.5

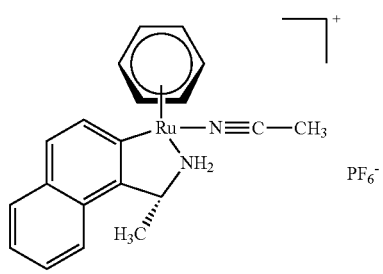

1.6

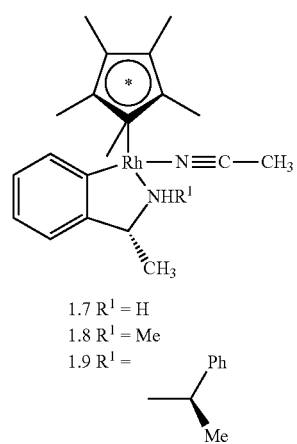

1.7 R¹ = H
1.8 R¹ = Me
1.9 R¹ = ⌬Ph/Me

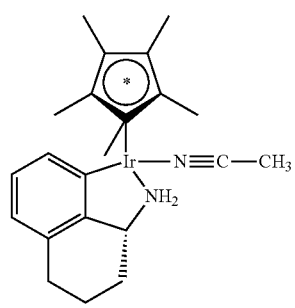

1.10

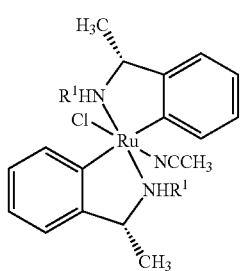

1.11

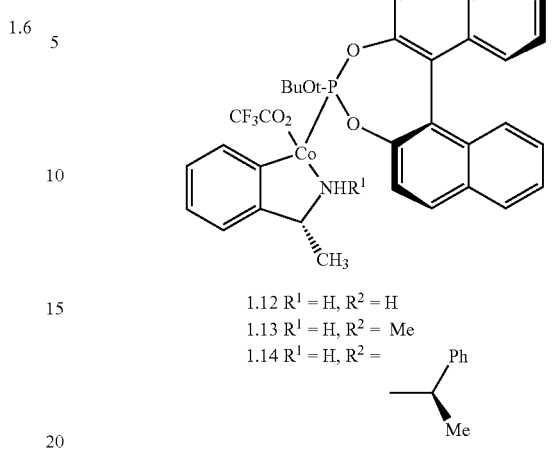

1.12 R¹ = H, R² = H
1.13 R¹ = H, R² = Me
1.14 R¹ = H, R² = ⌬Ph/Me

The chiral compound of formula 1 can further be made to be readily soluble in water or highly polar solvents. This is particularly preferred when the chiral compound is used as a catalyst. The chiral compounds of the invention according to formula 1 can be rendered water-soluble by introducing water-soluble groups in the cyclometallatable bidentate ligand, such as for instance, salts of carboxylic acids, salts of sulphonic acids and salts of phosphoric acids. Another possibility is the introduction of a trialkylammonium salt or a tetraalkylammonium salt in the cyclometallatable ligand. A third group of substituents that can be introduced into the cyclometallatable ligand are neutral polar groups of which there may be various present in the molecule, such as oligoethyleneglycol ethers, alcohols, sulphoxides, and the like. Another way of rendering the chiral compound of formula 1 water-soluble is to use bifunctional counter ions for the metal, for instance biscarboxylic acids, bisphosphates and bissulphonates. When a bifunctional counter ion is used, one of the two acid groups then serves as a counter ion for the metal M, while the other acid group is present as the salt of—for instance—sodium, potassium or lithium and may impart water solubility. It is also possible to introduce water-soluble groups on any one or more of $S^1$, $S^2$, $S^3$ or $S^4$.

The advantage of a water-soluble chiral compound according to formula 1 is that—when this compound is being used as a catalyst in a catalytic reaction, in particular in a transfer hydrogenation reaction—this reaction can be carried out in a two-phase system. In case of transfer hydrogenation, the two-phase system may for instance comprise a (more polar) aqueous phase and a (less polar or apolar) organic phase such as water/organic solvent, with the catalyst and an hydrogen donor being in the aqueous phase and the starting material and the product in the organic phase. As a result, the catalyst can very simply be separated from the product. A mixture of triethylamine and formic acid can also be chosen as the more polar phase. An example is the reduction of ketones in a two-phase system, with the more polar phase comprising an azeotropic mixture of triethylamine and formic acid, and the less polar phase comprising the ketone and the alcohol formed there off, optionally in the presence of a non-water-miscible solvent. At the end of the reaction the product can simply be separated by phase separation and the more polar phase can, after addition of extra formic acid, be reused in the reduction of a new batch of ketone. Another example of a more polar phase is an ionic liquid. Ionic liquids are characterized by the fact that they are liquids at room temperature.

Examples of ionic liquids are salts of imidazole such as 1-hexyl-3-methyl-imidazolium salts or N-alkyl pyridinium salts.

In addition, the invention relates to the use of the chiral and enantiomerically enriched compound according to the invention, preferably according to formula 1, wherein the transition metal M is to be chosen from groups 8, 9 and 10 of the Periodic Table of the Elements, in particular from iron, ruthenium, osmium, cobalt, rhodium, iridium, nickel, palladium or platinum, as a catalyst in, for example, an asymmetric transfer hydrogenation process, an asymmetric hydroformylation process, an asymmetric hydrogenation process, an asymmetric Michael addition, an asymmetric aldol condensation reaction, or an asymmetric oxidation reaction. Preferably, the compound is used as a catalyst in an asymmetric transfer hydrogenation process.

In particular, the catalysts of formula 1 can be advantageously used in transfer hydrogenation reactions of prochiral substrates/compounds as they give relatively high reaction rates. This makes it possible to use a relatively small amount of catalyst with respect to the substrate to be reduced.

Surprisingly, it has been found that the catalysts of the invention, based on easy accessible ligands, are rather robust and when used in transfer hydrogenation reactions, high yields and high enantioselectivities are obtained.

Catalysts based on ruthenium as the metal M are particularly preferred as these catalysts have a high activity in e.g. asymmetric transfer hydrogenation and yield products in relatively high e.e. Catalysts based on iron, nickel and cobalt as the metal M have the advantage that these are relatively inexpensive, of which iron has the additional advantage that it is environmentally friendly. Catalysts based on rhodium may for example be highly suitable when converting enones in an asymmetric transfer hydrogenation process. Catalysts based on palladium, ruthenium, rhodium and nickel are highly suitable since a variety of these metal precursors are commercially available.

The turnover frequency (TOF), which can be defined as the number of moles of product obtained per mol of catalyst used per hour, preferably is—when using the catalyst of the invention—at least about 10, more preferred at least about 30, even more preferred at least about 50, particularly preferred at least about 100 and most preferred at least about 200.

When using the catalyst of the invention in a catalytic reaction, preferably in asymmetric (transfer) hydrogenation of a prochiral compound, yields may be obtained of about 20% or higher, preferably about 40% or higher, more preferred about 70% or higher and most preferred about 85% or higher and enantiomerically enriched compounds can be obtained with an e.e. of at least about 10%, preferably at least about 30%, more preferred at least about 50%, even more preferred at least about 70%, particularly preferred at least about 90%, and most preferred at least about 95%. It is even possible to obtain the product in an e.e. of higher than about 98%.

In some cases, it may be desirable to activate the catalyst prior to use by the addition of acids, bases, or additives, such as for example silver salts or reducing agents such as sodium borohydride.

According to a preferred embodiment, the catalyst can be prepared in situ during the catalytic reaction, preferably during the asymmetric transfer hydrogenation reaction. Preferably, the catalyst of formula 1 is prepared in one particular solvent or solvent mixture and after a solvent switch to another solvent, for example a solvent which is also a hydrogen donating organic compound, such as for example isopropanol, is reacted further with the substrate that needs to be reduced. This has the advantage that the catalyst does not need to be isolated after preparation and therefore is highly suitable in a high throughput screening process. The principles of high throughput screening are known to a person skilled in the art and are, for example, disclosed in C. Gennari and U. Piarulli, Chem. Rev. 2003, 103, 3071-3100 and in J. G. de Vries and A. H. M. de Vries, Eur. J. Org. Chem. 2003, 799-713, which are incorporated herein by reference.

As a large number of primary and/or secondary amine compounds of formula 2 are commercially available in enantiomerically enriched form, preferably in enantiopure form, or can easily be prepared from the commercially available enantiomerically enriched, preferably enantiopure primary amine compounds by further functionalisation, a large library of chiral and enantiomerically enriched catalysts according to formula 1 can be prepared in parallel in a robot and immediately tested for activity and selectivity in the desired catalytic reaction, preferably in the desired transfer hydrogenation reaction.

Thus, the invention further relates to a screening process for finding a chiral compound suitable as a catalyst for a given catalytic transformation, preferably for an asymmetric transfer hydrogenation reaction, said process comprising contacting a transition metal precursor according to formula 3 with a library of cyclometallatable ligands according to formula 2, and optionally at least one additive and optionally at least one solvent, upon formation of an array of chiral compounds according to formula 1, and contacting said chiral compounds of said array with at least one substrate and at least one reagent, to identify a chiral compound having catalytic activity for a given catalytic transformation, preferably for an asymmetric transfer hydrogenation process. In particular, the preparation of the array of chiral compounds in the above screening process is in accordance with Scheme 1, using at least one reaction condition.

In such a screening process for finding a suitable catalyst for an asymmetric transfer hydrogenation reaction, an array of more than about 8, preferably more than about 10, more preferred more than about 20, even more preferred more than about 30 different catalysts according to formula 1 can be prepared in an automated device, such as a Zinnser Lissy. Preferably, after removal of the solvent that optionally is present during preparation of the catalyst of the invention, a prochiral substrate, an hydrogen donor and optionally, a solvent may be added after which the solution may be stirred for a certain time between 1 and 24 hours at a temperature between 23° C. and 60° C. This screening process is thus allowing very rapid evaluation of a large variety of catalysts (hereinafter referred to by "a library of catalysts") for the reduction of a given prochiral substrate. It will be clear to those skilled in the art that this method, which allows the screening of hundreds to thousands of different combinations of catalyst precursors of formula 3 and cyclometallatable ligands of formula 2 with different additives, solvents, hydrogen donors and under different conditions will greatly increase the chances of finding a highly enantioselective catalyst for a desired transformation. Thus this invention is of great importance in the field of fine chemicals and pharmaceuticals.

The invention further relates to a process for the asymmetric transfer hydrogenation of a prochiral compound (or substrate) in the presence of a hydrogen donor and the chiral and enantiomerically enriched catalyst according to the invention comprising a transition metal M which is to be chosen from groups 8, 9 and 10 of the Periodic Table, in particular chosen from iron, ruthenium, osmium, cobalt, rhodium, iridium, nickel, palladium, or platinum, upon which an enantiomerically enriched compound (or product) is formed from the corresponding prochiral compound (substrate).

The catalysts in which M is chosen from nickel, palladium, or platinum can be conveniently prepared in the manner as described above using metal precursors such as e.g. Pd(OAc)$_2$, [Pd(NO$_3$)$_2$], [PdCl$_2$ (CH$_3$CN)$_2$], Pd$_2$(dba)$_3$, (COD)PtBr$_2$, PtCl$_2$, PtCl$_2$(CH$_3$CN)$_2$, NiCl$_2$, NiBr$_2$, Ni(NO$_3$)$_2$.nH$_2$O, and the like.

The prochiral compound may be selected from the group consisting of ketones, imines, oxime derivatives, hydrazone derivatives, substituted enones and olefinically unsaturated compounds. The process can for instance very suitably be used in the preparation of enantiomerically enriched alcohols from the prochiral ketones, ketones or allylic alcohols from the prochiral enones, hydrazines from the prochiral hydrazones and amines from the corresponding prochiral oxime derivatives or imines. In case the catalyst contains a chiral metal M, the catalyst is not necessarily enantiopure on the metal.

The catalyst of the invention comprising a transition metal M chosen from iron, ruthenium, osmium, cobalt, rhodium, iridium, nickel, palladium, or platinum, can further advantageously be used for the kinetic resolution of carbonyl compounds—such as e.g. ketones, enones or aldehydes—or of imines, oximes or hydrazones, which already contain at least one chiral centre elsewhere in the molecule and are present as a mixture of both enantiomers, preferably in racemic form (i.e. 50/50 mixture of both enantiomers). Then, reduction of a C=O, or a C=N, or a C=C double bond (via an asymmetric transfer hydrogenation process) preferably takes place of only one of the two enantiomeric forms of the carbonyl compounds, imines, oximes or hydrazones. The ketone, enone, aldehyde, imine, oxime or hydrazone can be recovered substantially in the one enantiomeric form, whereas the other enantiomer has substantially been converted to the corresponding enantiomerically enriched alcohol, amine or hydrazine.

The invention further relates to a process for the preparation of an enantiomerically enriched compound with two or more chiral and enantiomerically enriched centres in which a chiral and enantiomerically enriched compound chosen from a ketone, enone, imine, oxime or hydrazone compound is reduced (via an asymmetric transfer hydrogenation process) in the presence of a catalyst according to the invention, whereby the metal M is chosen from iron, ruthenium, osmium, cobalt, rhodium, iridium, nickel, palladium, or platinum. In this process—which is hereinafter referred to as a diastereoselective process—the ketone, enone, imine, oxime or hydrazone is fully reduced to a compound with substantially only one relative configuration between the existing chiral and enantiomerically enriched centre(s) and the new chiral and enantiomerically enriched centre.

As prochiral compounds use can for instance be made of prochiral ketones of the general formula (4):

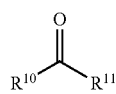

(4)

where $R^{10}$ and $R^{11}$ are different and each independently represent an alkyl, aryl, aralkyl, alkenyl or alkynyl group with 1-20 C-atoms or together form a ring along with the carbonyl C-atom to which they are bound, it being possible for $R^{10}$ and $R^{11}$ to also contain one or more heteroatoms or functional groups. Suitable examples of prochiral ketones include acetophenone, 1-acetonaphthone, 2-acetonaphthone, 3-quinuclidinone, 2-methoxycyclohexanone, 1-phenyl-2-butanone, benzyl-isopropyl ketone, benzyl acetone, cyclohexyl-methyl ketone, tert-butyl-methyl ketone, tert-butyl-phenyl ketone, isopropyl-phenyl ketone, ethyl-(n-propyl) ketone, o, m or p-methoxy acetophenone, o, m or p-(fluoro-, chloro-, bromo- or iodo-) acetophenone, o, m or p-cyano-acetophenone, o, m or p-nitro-acetophenone, 2-acetylfluorene, acetyl-ferrocene, 2-acetylthiophene, 3-acetylthiophene, 2-acetylpyrrole, 3-acetylpyrrole, 2-acetylfuran, 3-acetylfuran, 1-indanone, 2-hydroxy-1-indanone, 1-tetralone, p-methoxyphenyl-p'-cyanophenylbenzophenone, cyclopropyl-(4-methoxyphenyl) ketone, 2-acetylpyridine, 3-acetylpyridine, 4-acetylpyridine, acetylpyrazine; prochiral imines of the general formula (5):

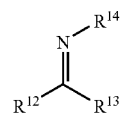

(5)

where $R^{12}$, $R^{13}$, $R^{14}$, for instance each independently represent an alkyl, aryl, aralkyl, alkenyl or alkynyl group with 1-20 C-atoms or form a ring together with the atoms to which they are bound, it being possible for $R^{12}$, $R^{13}$ and $R^{14}$ to also contain one or more heteroatoms and functional groups, and $R^{14}$ may in addition be a group to be split off, such as an alkylsulfonyl or a diarylphoshinyl group. Suitable prochiral imines may be prepared from the above-described ketones and an alkyl amine, aralkyl amine or aryl amine or an amino acid derivative, for instance an amino acid amide, an amino acid ester, a peptide or a polypeptide. Examples of suitable alkyl amines, aralkyl amines and aryl amines are a benzyl amine, for instance benzyl amine, or an o-, m- or p-substituted benzyl amine, an α-alkyl benzyl amine, a naphthyl amine, for instance naphthyl amine, a 1-, 2-, 3-, 4-, 6-, 7-, 8- or 9-substituted naphthyl amine and a 1-(1-naphthyl)alkyl amine or a 1-(2-phthyl)alkyl amine. Suitable imines are for instance N-(2-ethyl-6-methylphenyl)-1-methoxy-acetonimine, 5,6-difluoro-2-methyl-1,4-benzoxazine, 2-cyano-1-pyrroline, 2-ethyoxycarbonyl-1-pyrroline, 2-phenyl-1-pyrroline, 2-phenyl-3,4,5,6-tetrahydropyridine and 3,4-dihydro-6,7-dimethoxy-1-methyl-isoquinoline;

oximes or hydrazones of the general formula (6):

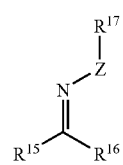

(6)

where
Z contains a heteroatom and represents NH, NR or O, for instance, with R representing an alkyl, aryl, aralkyl, alkenyl or alkynyl group with 1-20 C-atoms.
$R^{15}$ and $R^{16}$ each independently represent an alkyl, aryl, aralkyl, alkenyl or alkynyl group with 1-20 C-atoms, or form a ring with each other or with $R^{17}$ and the atoms to which they are bound, which groups may also contain one or more heteroatoms and/or functional groups.

in the case of an oxime or oxime ether, $R^{17}$ is H or an alkyl, aryl, aralkyl, alkenyl, alkynyl, acyl, phosphonyl or sulphonyl group with 1-20 C-atoms, which groups may also contain one or more heteroatoms and/or functional groups;

and in the case of a hydrazone it is H, an alkyl, aryl, alkenyl, alkynyl, acyl, phosphonyl or sulphonyl group with 0-20 C-atoms, which groups may also contain one or more heteroatoms and/or functional groups;

substituted enones of the general formula (7):

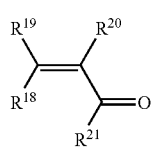

(7)

where $R^{18}$-$R^{21}$ each independently represent hydrogen, an optionally substituted alkyl or aryl group, and acetamido group, a thioether, and the like Either the olefinic function or the ketone of these enones will be reduced, depending on the metal used, with for instance rhodium having a preference for olefin hydrogenation and ruthenium for ketone hydrogenation. If the olefinic function is reduced, $R^{18}$ and $R^{19}$ may not be the same in case $R^{20}$ is hydrogen. If the ketone is hydrogenated, $R^{21}$ is not hydrogen. Suitable examples of prochiral enones are:

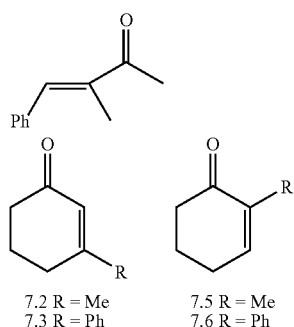

7.1

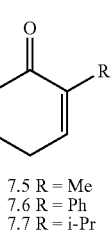

7.2 R = Me
7.3 R = Ph
7.4 R = i-Pr 7.5 R = Me
7.6 R = Ph
7.7 R = i-Pr

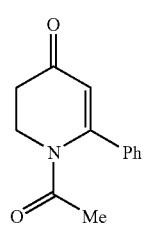

7.8

Preferably, the concentration of the prochiral compound is between 0.01 and 1.0 M, more preferably between 0.05 and 0.7 M, and most preferred between 0.1 and 0.6 mol per litre of the solvent and/or the hydrogen donor. Under these conditions the catalyst according to the invention has been found to be stable, in particular when ruthenium is used as the transition metal.

The process for the catalytic asymmetric transfer hydrogenation according to the invention is carried out in the presence of one or more hydrogen donors, which in the framework of this invention are understood to mean compounds that can in any way transfer hydrogen to the substrate, for instance thermally or catalytically. Examples of suitable hydrogen donors that can be used are aliphatic or aromatic alcohols, in particular secondary alcohols with 1-10 carbon atoms, for instance 2-propanol (or isopropanol), 2-butanol and cyclohexanol, acids, for instance formic acid, formic acids salts, hypophosphite, $H_3PO_2$, $H_3PO_3$ and salts thereof, partially unsaturated hydrocarbons, partially unsaturated heterocyclic compounds, hydroquinone or reducing sugars. Preferably, 2-propanol, formic acids or formic acid salts are used, of which formic acid in the form of its salt is more preferably used. A mixture of triethylamine $Et_3N$ and formic acid may also be used, in which case it is preferred not to use excess formic acid relatively to the $Et_3N$. The molar ratio of substrate to hydrogen donor preferably lies between 1:1 and 1:200.

In the asymmetric transfer hydrogenation use is preferably made of a molar ratio of metal present in the transition metal compound to substrate of between 1:10 and 1:1,000,000, in particular between 1:100 en 1:100,000.

The temperature at which the asymmetric transfer hydrogenation is carried out in general is a compromise between the reaction velocity on the one hand and the degree of racemisation on the other hand, and preferably lies between −20 and 100° C., in particular between 0 and 60° C. The asymmetric transfer hydrogenation is preferably carried out in an inert atmosphere, for instance under nitrogen.

As solvent in principle any solvent can be used that is inert in the reaction mixture. In a preferred embodiment a solvent is used that also serves as hydrogen donor, for instance 2-propanol. If the asymmetric transfer hydrogenation is carried out in water, with a 2-phase system being formed, preferably a water-soluble catalyst according to the invention is used. The catalyst for the asymmetric transfer hydrogenation can if desired be activated by hydrogenation with hydrogen or by treatment with a base, for instance an (earth) alkali compound, for instance an (earth) alkali hydroxide, an (earth) alkali carboxylate or an (earth) alkali alkoxide with 1-20 carbon atoms, as alkali metal for instance Li, Na or K being used and as (earth) alkali metal for instance Mg or Ca. Examples of suitable bases are for instance sodium hydroxide, potassium hydroxide, potassium-t-butoxide and magnesium methoxide. In general, however, such a treatment will not be necessary.

The invention will be elucidated with reference to the examples, without however being restricted thereto.

EXAMPLES

Examples 1-4

Processes for the Preparation of Cyclometallatable Bidentate Ligands According to Formula 2

Example 1

Preparation of N-isopropylphenethylamine (Compound 2.8 But with Opposite Configuration)

In a flask, a solution of (R)-1-phenethylamine in acetone (16 mmol/L) is heated to reflux. The imine formation is followed by GC. When the reaction is completed, the solvent is removed in vacuum after addition of a small amount of $Na_2SO_4$. After filtration, the imine is diluted in ethanol (40 mmol/L) and cooled to 0° C. with an ice bath. Then, three equivalents of $NaBH_4$ are slowly added to the solution. When the addition is finished, the mixture is slowly warmed to room temperature and stirred overnight. The amine formation is followed by GC. When the reaction is complete, a solution of HCl 1M is added to obtain a pH=1. Then, some toluene is added to the solution (100 mL/8 mmol of amine) and the solution is stirred during 20 min. After separation of the layers the solution is basified to pH=9 by a solution of NaOH 1M. Then, the solution is extracted three times by toluene and the organic layer is dried with $Na_2SO_4$. The solvent is removed in vacuum. The product is purified by filtration on silica. Yield=95%. The product is a yellow oil.

NMR: $CDCl_3$, 300 MHz: 1.17 (d, 6H); 1.42 (d, 3H); 2.95 (m, 1H); 4.32 (q, 1H)

Example 2

Preparation of
N-(2,6-dimethoxybenzyl)1-phenethylamine

In a flask, a solution of 2,6-dimethoxybenzaldehyde (1 eq.) and R-phenethylamine (1 eq.) in ethanol is stirred during 20 min. The formation of the imine is followed by GC. When the reaction is completed, the solution is cooled to 0° C. with an ice bath. Then 3 equivalents of $NaBH_4$ are slowly added. When the addition is completed, the solution is warmed to room temperature and is stirred over night. The formation of the amine is followed by GC. When the reaction is completed, the solution is acidified by a solution of HCl 1M to pH=1, and then some toluene is added (100 mL/8 mmol of amine). Then, the solution is basified to pH=9 with a solution of NaOH 1M. The solution is extracted three times with toluene and the organic layer is dried with $Na_2SO_4$. The solvent is removed in vacuum and the product is purified by filtration on silica.

The product is a colorless oil. Yield=94%.

NMR: $CDCl_3$, 300 MHz: 1.43 (d, 3H); 3.65 (s, 6H); 3.94 (s, 2H); 4.32 (q, 1H)

Example 3

Preparation of (R,R)
N-(1-naphth-1-ylethyl)-1-phenethylamine

In a Schlenk tube under $N_2$ a mixture of acetonaphthone (10 mmol) and R-1-phenethylamine (10 mmol.) is stirred in $Ti(iPrO)_4$ (30 mmol) as solvent. The reaction is followed by GC to control the formation of the imine. When the conversion is complete, the mixture is placed in a reactor with a catalytic amount of Pd/C 5% (360 mg for 10 mmol of imine) under 2 bars of $H_2$. The reduction is also followed by GC. When the reaction is finished, the mixture is basified by treatment with 1N NaOH to which results in complete hydrolysis of the Ti(iPrOH). After filtration the aqueous layer is extracted 3 times with toluene. The organic layer is dried over $Na_2SO_4$ and then the solvent is evaporated in vacuum. A yellow solid was obtained which was washed with pentane and filtrated. The R,R product was obtained with a purity of 99% and 36% yield as a white solid.

NMR: $CDCl_3$, 300 MHz: 1.34 (d, 3H); 1.44 (d, 3H); 4.52 (q, 3H); 4.75 (q, 3H)

Example 4

Preparation of (R) N-(2,6-dimethylbenzyl)-1-(1-naphthyl)ethylamine

The same method is used as for the preparation of N-(2,6-dimethoxybenzyl)phenethylamine as in Example 2. Use is now made of (R)-1-naphth-1-ylethylamine as starting amine and 2,6-dimethylbenzaldehyde as aldehyde. The product is a colorless oil. Yield=96%

NMR: $CDCl_3$, 300 MHz: 1.51 (d, 3H); 2.45 (s, 6H); 3.82 (s, 2H); 4.52 (q, 1H)

5. Process for the Preparation of the Chiral and Enantiomerically Enriched Compound (S)-[Ru($\eta^6$-$C_6H_6$){3-($NH_2$-$\kappa N$)—$C_{10}H_{10}$-$\kappa C^1$}(NCMe)($KPF_6$) according to formula 1.5.

A suspension of $[Ru(\eta^6-C_6H_6)Cl_2]_2$ (0.200 g, 0.4 mmol) as metal precursor, (S)-1-aminotetralin (0.56 mmol), NaOH (0.033 g, 0.83 mmol) and $KPF_6$ (0.29 g, 1.6 mmol) in $CH_3CN$ (6 mL) was stirred at 20° C. during 72 hours. The resulting dark-yellow suspension was filtered over $Al_2O_3$ using $CH_3CN$ as eluent. A yellow fraction was collected and concentrated in vacuo to ca. 2 mL $CH_2Cl_2$ (2 mL). diethyl ether (10 mL) was added to this solution, which afforded yellow crystals of the complex after standing in the fridge (0° C.) for several days. The compound is a mixture of diastereomers due to the chirality on the ruthenium. The compound is chiral and enantiomerically enriched in the cyclometallatable bidentate ligand.

$^1H$ NMR ($CDCl_3$, 400 MHz) of the two diastereomers:

$S_C$, $R_{Ru}$—[Ru($\eta^6$-$C_6H_6$){3-($NH_2$-$\kappa N$)—$C_{10}H_{10}$-$\kappa C^1$}(NCMe)($KPF_6$):

δ 7.5 (dd, 1H, H10, $^3J$=7.2, $^4J$=0.7), 7.01 (td, 1H, H9, $^3J$=7.4, $^5J$=0.7), 6.78 (dd, 1H, H8, $^3J$=7.5, $^4J$=0.5), 5.60 (s, 6H, $C_6H_6$), 5.24 (dd, 1H, NH, $^2J$=10.6), 3.61 (m, 1H, H3), 2.66 (m, 3H, H6 and NH), 2.41 (m, 1H, H4), 2.24 (s, 3H, $CH_3CN$), 1.96 (m, 1H, H5), 1.66 (m, 1H, H5), 1.48 (m, 1H, H4).

$S_C$, $S_{Ru}$—[Ru($\eta^6$-$C_6H_6$){3-($NH_2$-$\kappa N$)—$C_{10}H_{10}$-$\kappa C^1$}(NCMe)($KPF_6$):

δ 7.85 (dd, 1H, H10, $^3J$=6.6, $^4J$=0.8), 7.02 (td, 1H, H9, $^3J$=7.5, $^5J$=0.8), 6.79 (dd, 1H, H8, $^3J$=7.5, $^4J$=1.0), 5.58 (s, 6H, $C_6H_6$), 4.67 (dd, 1H, NH, $^2J$=10.6), 4.02 (t, 1H, NH, $^2J$=$^3J$=10.9), 3.54 (m, 1H, H3), 2.66 (m, 2H, H6), 2.41 (m, 1H, H4), 2.30 (s, 3H, $CH_3CN$), 1.96 (m, 1H, H5), 1.66 (m, 1H, H5), 1.48 (m, 1H, H4).

Experiments 6-16 Catalytic Transfer Hydrogenation of Acetophenone in Schlenk Tubes with Pre-formed Chiral Ruthenium Compounds According to Formula 1 as Catalysts The catalyst is first prepared via a process analogue to the process described in Example 5 (pre-formed catalyst), with the difference in work-up: after the reaction, the solvent was removed in vacuo to yield the catalyst as a powder.

The catalyst (10 μmol) was dissolved in 2-propanol (10 mL) under argon, and acetophenone (120 mg, 1 mmol) was added, followed by tBuOK (5.6 mg, 50 μmol). The reaction was periodically monitored by GC. When it was finished, the crude product was chromatographically purified over silica gel using $Et_2O$ as eluent. The yields and e.e. values were determined by GC using a chiral capillary column (Chiraldex β-PM, 50 m×0.25 mm). Results for the different catalysts are given in Table 1.

TABLE 1

Asymmetric transfer hydrogenation of acetophenone with pre-formed chiral ruthenium compounds according to formula 1

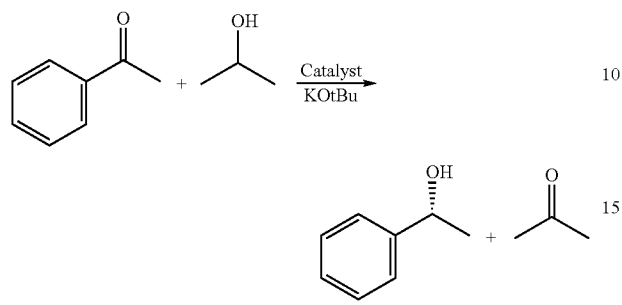

| Ex | Catalyst | Temp. (° C.) | Time (h) | Yield (%) | e.e. (%) |
|---|---|---|---|---|---|
| 6 | 1.1 | 20 | 2 | 92 | 38 |
| 7 | 1.1 | 0 | 7 | 65 | 39 |
| 8 | 1.2 | 20 | 0.5 | 96 | 10 |
| 9 | 1.2[a] | 20 | 22 | 8 | 10 |
| 10 | 1.2[b] | 20 | 6 | 96 | 12 |
| 11 | 1.3 | 20 | 0.5 | 96 | 76 |
| 12 | 1.3 | 0 | 2 | 95 | 85 |
| 13 | 1.4 | 20 | 1 | 94 | 52 |
| 14 | 1.4[b] | 20 | 5 | 83 | 54 |
| 15 | 1.5 | 20 | 5 | 90 | 50 |
| 16 | 1.6 | 20 | 1 | 100 | 61 |

[a]Reaction run without base tBuOK.
[b]Reaction run with 0.5 µmol of catalyst

Experiments 17-35 High-Throughput Catalytic Transfer Hydrogenation Using In-situ Prepared Chiral Ruthenium Compounds According to Formula 1 as Catalyst A stock solution of [Ru($\eta^6$-arene)Cl$_2$]$_2$ (10.8 mM) as ruthenium precursor, NaOH (11.3 mM), and KPF$_6$ (22 mM) in acetonitrile was prepared under argon. Using a Zinnser Lizzy apparatus, the catalyst solutions were prepared in the following way: 1 mL of this stock solution was mixed with 1 mL of a 10 mM amine (cyclometallatable bidentate ligand of formula 2) solution in acetonitrile, followed by stirring at 40° C. for 5 hours. The solvent was then removed by flushing nitrogen at 40° C. for 16 hours. The residue, which contains the ruthenium-based catalyst according to formula 1, was dissolved in 2-propanol (4 mL) under nitrogen. 1 mL of a 560 mM acetophenone solution and 1 mL of a 15 mM tBuOK solution in 2-propanol were successively added. The solution was stirred at room temperature for 4.5 hours, then 0.3 mL glacial acetic acid was added to stop the reaction. An aliquot of 0.1 mL was diluted in 1 mL EtOAc and submitted to GC analysis. The conversions and e.e. values were determined by GC using a chiral capillary column (Chrompack CP-Sil 5CB, 25 m×0.25 mm). The methodology as followed is depicted in Scheme 2 below and the results for the different cyclometallatable ligands (amines) and different ruthenium precursors are depicted in Table 2.

Scheme 2. Methodology for High Throughput Screening of Enantioenriched Amines as Cyclometallated Ligands in the Transfer Hydrogenation of Acetophenone as Followed for Examples 17-35.

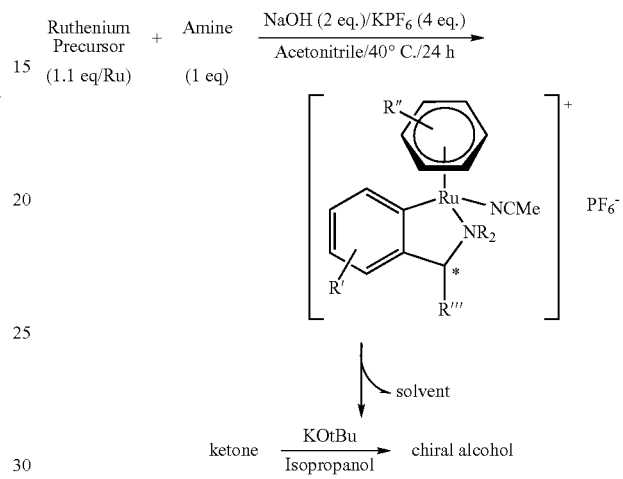

Within the spirit of the present invention, this methodology of Scheme 2 is applicable in general for high throughput screening processes according to the invention for finding a suitable catalyst for a given catalytic transformation whereby any metal precursor, any cyclometallatable ligand, any base, any additive, any solvent, and with different ratios and under different conditions may be used as described throughout this application.

TABLE 2

High-throughput screening of chiral amines in ruthenium-catalyzed asymmetric transfer hydrogenation of acetophenone as substrate (or prochiral compound)

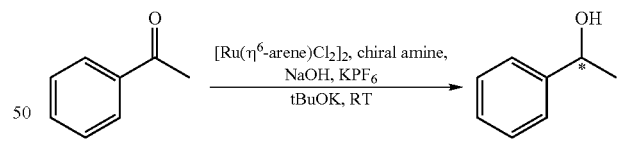

| Ex. | amine | Arene of the metal precursor | yield/% | e.e./%[a] |
|---|---|---|---|---|
| 17 | 2.1 | benzene | 79 | 38(S) |
| 18 | 2.1 | p-cymene | 10 | 37(S) |
| 19 | 2.9 | benzene | 86 | 54(S) |
| 20 | 2.9 | p-cymene | 5 | 56(S) |
| 21 | 2.10 | benzene | 90 | 50 |
| 22 | 2.12 | benzene | 96[b] | 69 |
| 23 | 2.12 | benzene | 20[b],[c] | 86 |
| 24 | 2.13 | p-cymene | 38 | 25(S) |
| 25 | 2.21 | benzene | 24 | 22(S) |
| 26 | 2.21 | p-cymene | 12 | 3(S) |
| 27 | 2.26 | benzene | 41 | 30(R) |
| 28 | 2.26 | p-cymene | 30 | 25(S) |
| 29 | 2.32 | benzene | 8 | 10(S) |
| 30 | 2.32 | p-cymene | 35 | 24(S) |
| 31 | 2.33 | benzene | 99 | 80(S) |

TABLE 2-continued

High-throughput screening of chiral amines in ruthenium-catalyzed asymmetric transfer hydrogenation of acetophenone as substrate (or prochiral compound)

| Ex. | amine | Arene of the metal precursor | yield/% | e.e./%[a] |
|-----|-------|------------------------------|---------|-----------|
| 32 | 2.33 | p-cymene | 79 | 44(S) |
| 33 | 2.36 | benzene | 21[b] | 76 |
| 34 | 2.35 | benzene | 49[b] | 89 |
| 35 | 2.61 | benzene | 75 | 70 |

[a]The absolute configuration of the major enantiomer is given between parentheses.
[b]After 1 hour
[c]At 0° C.

Example 36

Preparation of [($\eta^5$-C$_5$Me$_5$)Rh(C$_6$H$_4$-2-CH(Me)NH$_2$)(CH$_3$CN)]PF$_6$ A suspension of [Rh($\eta^5$-C$_5$Me$_5$)Cl$_2$]$_2$ (0.247 g, 0.4 mmol), the (R)-1-phenylethylamine (51 μL, 0.4 mmol), NaOH (0.03 g, 0.75 mmol), and KPF$_6$ (0.29 g, 1.57 mmol) in CH$_3$CN (6 mL) was stirred at 20° C. safe from light during 72 h. The resulting dark orange suspension was vigorously stirred with 20 mL of hexane during 2 hours. The CH$_3$CN layer was concentrated in vacuo and filtered over standardized Al$_2$O$_3$ (8×3 cm) using CH$_3$CN as eluent. An orange fraction was collected and evaporated in vacuo (113 mg, 58%). The resulting residue was redissolved in a minimum of CH$_3$CN (0.5 mL), CH$_2$CL$_2$ (0.5 mL) and diethyl ether (10 mL) were added to this solution to give an orange solid after standing overnight in the fridge (−15° C.). The solvents were removed and the solid was dried in vacuo.

$^1$H NMR (300 MHz, CD$_3$CN, 20° C.): δ=1.48 (d, 3H, $^3$J$_{HH}$=4.5 Hz, C(H)Me), 1.67 (s, 15H, $\eta^5$-C$_5$Me$_5$), 1.96 (s, 3H, CH$_3$CN), 3.27 (s, 1H, NH), 3.93 (s, 1H, NH), 4.28 (s, 1H, CH(Me)), 6.84-7.10 (m, 3H, H$_{arom}$), 7.45 (dd, $^3$J$_{HH}$=7.4 Hz, $^4$J$_{HH}$=1.3 Hz, 1H, H$_{ortho/Rh}$) ppm.

Example 37

Preparation of [($\eta^5$-C$_5$Me$_5$)Ir(C$_6$H$_4$-2-CH(Me)NH)(CH$_3$CN)]PF$_6$ A suspension of [Ir($\eta^5$-C$_5$Me$_5$)Cl$_2$]$_2$ (0.120 g, 0.15 mmol), the (R)-1-phenylethylamine (51 μL, 0.3 mmol), NaOH (0.012 g, 0.3 mmol), and KPF$_6$ (0.11 g, 0.6 mmol) in CH$_3$CN (4 mL) was stirred at 45° C. safe from light during 50 h. The resulting dark orange suspension was vigorously stirred with 20 mL of hexane during 2 hours. The CH$_3$CN layer (only 3% of free amine left) was concentrated in vacuo and filtered over standardized Al$_2$O$_3$ (8×3 cm) using CH$_3$CN as eluent. An orange fraction was collected and evaporated in vacuo (63%). The resulting residue was redissolved in a minimum of CH$_3$CN (2 mL), and diethyl ether (10 mL) was added to this solution to give an orange solid after standing overnight in the fridge (−15° C.). The solvents were removed and the solid was dried in vacuo.

Example 38

Preparation of [($\eta^5$-C$_5$Me$_5$)Rh(C$_6$H$_4$-2-CH(Me)NH$_2$)(Cl)]

The catalyst of Example 36 was dissolved in dichloromethane (1M) an equal volume of a saturated KCL solution was added and the mixture was vigorously stirred under argon for 18 h. After separation of the layers the dichloromethane solution was evaporated to give an orange solid (100% yield) which was the title compound.

Example 39

The catalyst prepared according to Example 36 (10 μmol) was dissolved in degassed 2-propanol (10 mL) under argon, and acetophenone (120 mg, 1 mmol) was added, followed by tBuOK (5.6 mg, 50 μmol). The reaction was periodically monitored by GC. When it was finished, the crude product was chromatographically purified over silica gel using Et$_2$O as eluent. The yields and e.e. values were determined by GC using a chiral capillary column (Chiraldex β-PM, 50 m×0.25 mm). Conversion after 2 h was 89% and e.e. was 34%.

Example 40

This Example was the same as Example 39 except for the fact that [($\eta^5$-C$_5$Me$_5$)Rh(C$_6$H$_4$-2-CH(Me)NH$_2$)(Cl)] was used as catalyst. Conversion was 95% after 1 h and the e.e. of the product 1-phenylethanol was 34%

Example 41

This Example was the same as Example 39 except that the catalyst of Exp 37 was used. Conversion of acetophenone was 10% after 1 h.

Example 42

The catalyst of formula 1.3 (10 μmol) was added to 1 mmol of acetophenone and tBuOK (5.6 mg, 50 μmol). Now 2.5 ml of 1M sodium formiate was added and the solution was stirred under nitrogen at 40° C. for 24 h. Conversion of acetophenone was 27%

Example 43

The catalyst of formula 1.3 (10 μmol) was added to 1 mmol of acetophenone and tBuOK (5.6 mg, 50 μmol). Now 2.5 ml of a HCO$_2$H/Et$_3$N (1.2:1) mixture was added and the solution was stirred under nitrogen at $_{40}$° C. for 24 h. Conversion of acetophenone was 6% and the e.e. was 40%

Example 44

The catalyst of formula 1.3 (10 μmol) was added to N-benzyl acetophenone imine (1 mmol) and tBuOK (5.6 mg, 50 μmol) was added too. Now 0.5 ml of a HCO$_2$H/Et$_3$N (3:2) mixture was added and the solution was stirred under nitrogen at 400 C for 24 h. After 36 h at ambient temperature 23% N-benzyl-1-phenylethylamine had formed.

Example 45

This Example was the same as Example 44 except that 6,7-dimethoxy-1 methyl-3,4-dihydroisoquinoline was used as substrate and a HCO₂H/Et₃N (5:2) mixture as reductant. After 3 h at ambient temperature a conversion of 31% to the amine was achieved.

The invention claimed is:

1. An enantiomerically enriched chiral compound comprising a transition metal M, which comprises four, five or six coordinating groups of which at least one pair is linked together to form a bidentate ligand, in which M is directly bound via one single σ-bond to a carbon atom of an optionally substituted and/or optionally fused (hetero)aromatic ring of said bidentate ligand and in which M is directly bound to a nitrogen atom of a primary or secondary amino group of said bidentate ligand, thereby forming a metallacycle between said bidentate ligand and the metal M, said metal M being selected from iron, ruthenium, osmium, cobalt, rhodium, or iridium.

2. A chiral compound according to claim 1, the compound being represented by any one of the formulae 1 a, 1 b or 1 c,

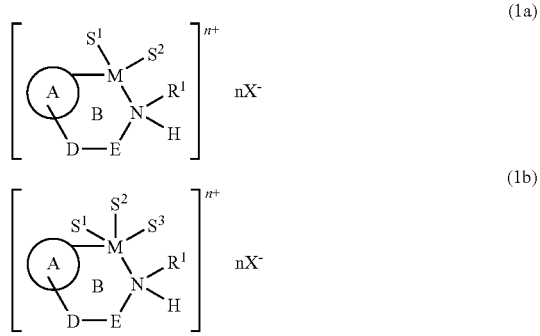

wherein said bidentate ligand comprises the optionally substituted and/or optionally fused (hetero)aromatic ring A and the amino group —NR¹H, wherein the nitrogen of the amino group is bound to the ring A via a fragment D-E, wherein each of D and E are independently chosen from the group consisting of a bond, an optionally substituted methylene group $CR^2R^3$, an optionally substituted ethylene group $CR^4R^5CR^6R^7$, an optionally substituted vinyl group $CR^8=CR^9$, said $CR^8=CR^9$- group optionally being part of an aromatic ring, or a heteroatom, wherein $R^1$, $R^2$, $R^3$, $R^4$, $R^5$, $R^6$, $R^7$, $R^8$ and $R^9$ are each independently selected from hydrogen, an optionally substituted carbon-, oxygen-, or nitrogen-substituent, X is a non-coordinating anion, n is 0, 1 or 2, and $S^1$, $S^2$, $S^3$ and $S^4$ are coordinating groups.

3. A compound according to claim 2, wherein (i) at least one of the atoms of and/or at least one of the substituents on said bidentate ligand is chiral and enantiomerically enriched, or (ii) at least one of the coordinating groups $S^1$, $S^2$, $S^3$ or $S^4$ is chiral and enantiomerically enriched, or (iii) the metal M is chiral and enantiomerically enriched, said chiral compound comprising at least one of (i), (ii) or (iii).

4. A compound according to claim 1, wherein at least one of D or E is chiral and enantiomerically enriched or contains a chiral and enantiomerically enriched substituent.

5. A compound according to claim 1, wherein the transition metal M is ruthenium.

6. A compound according to claim 1, wherein at least one of $S^1$, $S^2$, $S^3$ or $S^4$ is an aromatic compound.

7. Process for the preparation of a chiral compound as defined in claim 1, said process comprising reacting a metal precursor comprising a transition metal chosen from iron, ruthenium, osmium, cobalt, rhodium, or iridium with a cyclometallatable ligand according to formula 2,

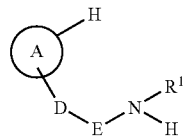

Formula 2 in the presence of a solvent, and optionally a base and or an additive.

8. A catalyst which comprises a chiral and enantiomerically enriched compound as defined in claim 1, wherein the metal M is chosen from iron, ruthenium, osmium, cobalt, rhodium, iridium, nickel, palladium or platinum.

9. A catalyst according to claim 8, wherein the catalyst is capable of catalyzing an asymmetric transfer hydrogenation process.

10. Process for the preparation of an enantiomerically enriched compound from a corresponding prochiral compound in which the prochiral compound is subjected, in the presence of a hydrogen donor, and a catalyst, and optionally a base, to an asymmetric transfer hydrogenation reaction, wherein said catalyst is a chiral and enantiomerically enriched compound as defined in claim 1 comprising a metal M which is chosen from iron, ruthenium, osmium, cobalt, rhodium, iridium, nickel, palladium or platinum.

11. Process for the kinetic resolution of a chiral compound, chosen from the group of ketones, enones, aldehydes, imines, oximes or hydrazones, in which a mixture of enantiomers of said chiral compound is subjected, in the presence of a catalyst, a hydrogen donor, and optionally a base, to an asymmetric transfer hydrogenation process, wherein said catalyst is a chiral and enantiomerically enriched compound as defined in claim 1 comprising a metal M that is chosen from iron, ruthenium, osmium, cobalt, rhodium, iridium, nickel, palladium or platinum.

* * * * *